US008188126B2

(12) United States Patent
Vacher et al.

(10) Patent No.: US 8,188,126 B2
(45) Date of Patent: May 29, 2012

(54) IMIDAZOLIC COMPOUNDS AND USE THEREOF AS ALPHA-2 ADRENERGIC RECEPTORS

(75) Inventors: Bernard Vacher, Castres (FR); Bernard Bonnaud, Lagarrigue (FR); Marc Marien, Castres (FR); Peter Pauwels, Chessenaz (FR)

(73) Assignee: Pierre Fabre Medicament, Boulogne (FR)

( * ) Notice: Subject to any disclaimer, the term of this patent is extended or adjusted under 35 U.S.C. 154(b) by 23 days.

(21) Appl. No.: 12/785,708

(22) Filed: May 24, 2010

(65) Prior Publication Data

US 2011/0021589 A1 Jan. 27, 2011

Related U.S. Application Data

(63) Continuation-in-part of application No. 11/783,079, filed on Apr. 5, 2007, now Pat. No. 7,776,901, which is a continuation of application No. 10/514,487, filed as application No. PCT/FR03/01476 on May 15, 2003, now Pat. No. 7,220,866.

(30) Foreign Application Priority Data

May 16, 2002 (FR) .................................... 02 06026

(51) Int. Cl.
*A61K 31/4164* (2006.01)
(52) U.S. Cl. ........................................................ 514/369
(58) Field of Classification Search .................. 514/396
See application file for complete search history.

(56) References Cited

U.S. PATENT DOCUMENTS

| 5,173,502 | A | 12/1992 | Malen et al. |
| 5,281,607 | A | 1/1994 | Stone et al. |
| 5,380,742 | A | 1/1995 | Sevrin et al. |
| 5,661,172 | A | 8/1997 | Colpaert et al. |
| 5,663,167 | A | 9/1997 | Pickar et al. |
| 5,948,806 | A | 9/1999 | Colpaert et al. |
| 6,153,638 | A | 11/2000 | Marien et al. |
| 6,610,725 | B1 | 8/2003 | Imbert et al. |
| 2002/0013356 | A1 | 1/2002 | Ratilainen et al. |

FOREIGN PATENT DOCUMENTS

| EP | 0183492 A1 | 6/1985 |
| EP | 0247764 A1 | 12/1987 |
| EP | 0486385 A1 | 5/1992 |
| EP | 0599697 A1 | 6/1994 |
| FR | 2735776 A1 | 12/1996 |
| FR | 2789681 A1 | 8/2000 |
| FR | 2795727 A1 | 1/2001 |
| GB | 2225782 A | 6/1990 |
| WO | WO 91/18886 A1 | 12/1991 |
| WO | WO 93/13074 A1 | 7/1993 |
| WO | WO 94/13285 A1 | 6/1994 |
| WO | WO 94/15603 A1 | 7/1994 |
| WO | WO 95/00145 A1 | 1/1995 |
| WO | WO 95/00492 A1 | 1/1995 |
| WO | WO 95/01791 A1 | 1/1995 |
| WO | WO 98/06393 A1 | 2/1998 |
| WO | WO 98/35670 A1 | 8/1998 |
| WO | WO 99/51593 A1 | 10/1999 |
| WO | WO 01/85698 A1 | 11/2001 |

OTHER PUBLICATIONS

Y. Amemiya et al., "Synthesis and α-Adrenergic Activities of 2- and 4-Substituted Imidazoline and Imidazole Analogues," American Chemical Society 750-755 (1992).
R. Bartus, "On Neurodegenerative Diseases, Models, and Treatment Strategies: Lessons Learned and Lessons Forgotten a Generation Following the Cholinergic Hypothesis," 163 Experimental Neurology 495-529 (2000).
E. Bezard et al., "Effect of the α2 Adrenoreceptor Antagonist, Idazoxan, On Motor Disabilities In MRTP-Treated Monkey," 23 Progress in Neuro-Psychopharmacology and Biological Psychiatry 1237-1246 (1999).
A. Charette et al., "New Family of Cyclopropanating Reagents: Synthesis, Reactivity, and Stability Studies of Iodomethylzinc Phenoxides," 39(24) Angewandte Chemie International Edition 4539-4541 (2000).
C. Chau et al, "Effects of Intrathecal $\alpha_1$- and $\alpha_2$-Noradrenergic Agonists and Norepinephrine on Locomotion in Chronic Spinal Cats," 79(6) Journal of Neurophysiology 2941-2963 (1998).
P. Chopin et al., "Effects of four non-cholinergic cognitive enhancers in comparison with tacrine and galanthamine on scopolamine-induced amnesia in rats," 106(1) Psychopharmacology 26-30 (1992).
A. Cordi et al., "Synthesis and structure-activity of 4(5)-(2,2-diphenylethyl)imidazoles as new $\alpha_2$-adrenoreceptor antagonists," 25 European Journal of Medical Chemistry 557-568 (1990).
J. Coull et al., "The $\alpha_2$ antagonist idazoxan remediates certain attentional and executive dysfunction in patients with dementia of frontal type," 123(1) Psychopharmacology 239-249 (1996).

(Continued)

*Primary Examiner* — Shawquia Young
(74) *Attorney, Agent, or Firm* — Buchanan Ingersoll & Rooney PC

(57) ABSTRACT

The invention provides methods of treating a memory deficiency in a subject in need of such treatment, where the methods comprise administering to a subject an effective amount of a compound of formula (1):

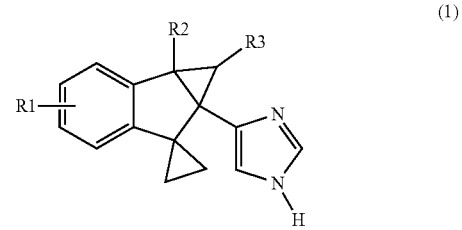

wherein: R1 is hydrogen, fluorine or a methoxyl group, R1 being in position 2, 3, 4 or 5 of the aromatic carbocycle; R2 is hydrogen or a methyl group; R3 is hydrogen, a methyl group or an ethyl group; and their pharmaceutically acceptable acid addition salt as well as the isomers and the tautomers thereof. The memory deficiency may be correlated with a memory deficiency induced by scopolamine.

7 Claims, No Drawings

OTHER PUBLICATIONS

R. Davis, "Therapeutic strategies to retard neuronal cell death in neurodegenerative diseases," 2(5) Current Opinion in Investigational Drugs 654-656 (2001).

U. Ebert et al., "Scopolamine model of dementia: electroencephalogram findings and cognitive performance," 28 European Journal of Clinical Investigation 944-949 (1998).

F. Gage at al., "Regional Changes in Brain Glucose Metabolism Reflect Cognitive Impairments in Aged Rats," 4(11) The Journal of Neuroscience 2856-2865 (Nov. 1984).

J. Grutzendler et al., "Cholinesterase Inhibitors for Alzheimer's Disease," 61(1) Drugs 41-52 (2001).

I. Gustafson et al., "Protection Against Ischemia-Induced Neuronal Damage by the $\alpha_2$-Adrenoceptor Antagonist Idazoxan: Influence of Time of Administration and Possible Mechanisms of Action," 10 Journal of Cerebral Blood Flow and Metabolism 885-894 (1990).

P. Heinonen et al., "Synthesis and pharmacological properties of 4(5)-(2-ethyl-2,3-dihydro-2-silainden-2-yl)imidazole, a silicon analogue of atipamezole," 31 European Journal of Medical Chemistry 725-729 (1996).

D. Horne et al., "A Two-Step Synthesis of Imidazoles From Aldehydes Via 4-Tosyloxazolines" 39(1) Heterocycles 139-153 (1994).

B. Leplow et al., "Spatial behaviour is driven by proximal cues even in mildly impaired Parkinson's disease," 40 Neuropsychologia 1443-1455 (2002).

P. Mayer et al., "$\alpha_2$-Adrenoceptor antagonists," 4(6) IDrugs 662-673 (2001).

R. Mayeux et al., "Treatment of Alzheimer's Disease," 341(22) The New England Journal of Medicine 1670-1679 (Nov. 25, 1999).

M. M'Harzi et al., "Effects of RU 52583, an $\alpha$2-antagonist, on Memory in Rats With Excitotoxic Damage to the Septal Area," 56(4) Pharmacology Biochemistry and Behavior 649-655 (1997).

R. Morris, "Spatial Localization Does Not Require the Presence of Local Cues," 12 Learning and Motivation 239-260 (1981).

S. Nakamura, "Effects of mianserin and fluoxetine on axonal regeneration o brain catecholamine neurons," 2 NeuroReport 525-528 (1991).

V. Pickel et al., "A Radioautographic Study of the Efferent Pathways of the Nucleus Locus Coeruleus," 155 Journal of Comparative Neurology 15-42 (May 1, 1974).

B. Postle et al., "The time course of spatial and object learning in Parkinson's disease," 35(10) Neuropsychologia 1413-1422 (1997).

B. Postle et al., "Spatial, but Not Object, Delayed Response Is Impaired in Early Parkinson's Disease," 11(2) Neuropsychology 171-179 (1997).

H. Sugimoto, "Donepezil Hydrochloride: A Treatment Drug for Alzheimer's Disease," 1 The Chemical Record 63-73 (2001).

J. Tassin et al., "Collateral Sprouting and Reduced Activity of the Rat Mesocortical Dopaminergic Neurons After Selective Destruction of the Ascending Noradrenergic Bundles," 4 Neuroscience 1569-1582 (1979).

A. van Leusen et al., "Synthesis of 1-isocyano-1-tosyl-1-alkenes and their use in the preparation of imidazoles," Recueil des Travaux Chimiques des Pays-Bas 258-262 (1979).

L. Yavich et al., "The systemic administration of tacrine or selegiline facilitate spatial learning in aged fisher 344 rats," 103 Journal of Neural Transmission 619-626 (1996).

E. Zurad, "New Treatments of Alzheimer Disease: A Review," Behavioral Health Trends 27-40.

Cecil Textbook of Medicine, 20th Edition (1996), vol. 2, pp. 2050-2057.

Cecil Textbook of Medicine, 20th Edition (1996), vol. 2, pp. 1992-1996.

FDA mulls drugs to slow late-stage Alzheimer's (online), retrieved on Sep. 23, 2003). Retrieved from the Internet, URL: http://www.cnn.com/2003/HEALTH/conditions/09/24/alzheimers.drug.ap/index.html>.

Neurodegenerative disease (online), (retrieved on Jul. 21, 2006). Retrieved from the internet, URL: http://en.wikipedia.org/wiki/Neurodegenerative_disease>.

Huntington's disease (online) retrieved on Sep. 10, 2009 from the internet (<URL:http://www.healthline.com/adamcontent/huntgontons-disease>).

Memory Loss (online) (retrieved on Sep. 4, 2008)(URL:http://www..nih.gov/medlineplus/ency/article/003257.htm).

Vippagunta et al., Advanced Drug Delivery Reviews 48 (2001)3-26.

Isomers (onoline), (retrieved on Mar. 11, 2007). Retrieved from Internet, URL: http://chemed.purdue.edu/genchem/topicreview/bp/1organic/isomers.html>.

International Search Report for PCT/FR03/01476 issued Oct. 14, 2003.

IMIDAZOLIC COMPOUNDS AND USE THEREOF AS ALPHA-2 ADRENERGIC RECEPTORS

CROSS REFERENCE TO PRIOR APPLICATIONS

This application is a continuation-in-part application of U.S. application Ser. No. 11/783,079, filed on Apr. 5, 2007, now allowed, which is a continuation Application of U.S. application Ser. No. 10/514,487, filed on Sep. 22, 2005, now U.S. Pat. No. 7,220,866, which was the National Stage of International Application No. PCT/FR03/01476, filed May 15, 2003, and claims priority under 35 U.S.C. §119(a)-(d) of French Patent Application No. 02/06026, filed May 16, 2002, said applications being incorporated by reference herein in their entireties and relied upon.

The present invention relates to new imidazolic compounds. The derivatives according to the invention interact selectively with pre and/or post-synaptic alpha-2 type adrenergic receptors (J. Neurochem. 2001, 78, 685-93) on which they behave as partial agonists, antagonists or reverse agonists. As such, the compounds according to the invention are therefore potentially useful in the treatment of diseases or conditions susceptible to adrenergic regulation controlled by alpha-2 adrenergic receptors. The list of diseases considered as susceptible to such regulation is excessively long. However, the scope of the present invention is restricted to the treatment of neurodegenerative diseases and the treatment of the progression thereof (Psychopharmacology 1996, 123(3), 239-49; Prog. Neuro-Psychopharmacol. Biol. Psychiatry 1999, 23(7), 1237-46; U.S. Pat. No. 5,663,167; FR 2789681; WO 9835670; WO 9806393; WO 9500145; WO 9413285; WO 9118886), particularly the treatment of Alzheimer's disease or the treatment of the progression thereof (U.S. Pat. No. 5,281,607; FR 2795727; WO 9501791; WO 9415603).

Alzheimer's disease is the most widespread progressive degenerative disease in the elderly population. It is estimated that over 15 million people are affected (New Engl. J. Med. 1999, 341(22), 1670-79; Drug Benefit Trends 2001, 13/7, 27-40). Acetylcholinesterase inhibitors (e.g. tacrine, donepezil, rivastigmine and galantamine) represent, at the present time, the only symptomatic treatment of this disease. However, the therapeutic benefits obtained are modest at the very mode (Drugs 2001, 61/1, 41-52). Since effective therapeutic strategies against Alzheimer's disease are limited (Curr. Opin. Invest. Drugs 2001, 2(5), 645-56), the discovery of new treatments using molecules with a different mode of action to that of the molecules currently available in clinical practice and capable of treating or delaying the progression of the disease is therefore highly desirable.

It has been demonstrated, in vitro and on animals, that a substance activating the noradrenergic system may, firstly, inhibit the progression of neuronal degeneration (J. Neurophysiol. 1998, 79(6), 2941-63; Pharmacol. Biochem. Behav. 1997, 56(4), 649-55; J. Cereb. Blood Flow Metabolism 1990, 10(6), 885-94) and, secondly, stimulate neuronal growth (J. Comp. Neurol. 1974, 155(1), 15-42; Neuroscience 1979, 4(11), 1569-82; Neuroreport 1991, 2, 528-8). As a result, compounds with partial agonistic, antagonistic or reverse antagonistic properties on alpha-2 adrenergic receptors, particularly on pre-synaptic alpha-2 receptors, may be useful in the treatment of neurodegenerative diseases. In view of the therapeutic potential of compounds with partial agonistic, antagonistic or reverse antagonistic properties for alpha-2 adrenergic receptors, the discovery of new structures having such properties is highly desirable. As such, the applicant discovered that new imidazolic derivatives interact selectively with alpha-2 subtype adrenergic receptors on which they behave as partial agonists, antagonists or reverse agonists.

Numerous pre and/or post-synaptic antagonists and/or partial agonists of alpha-2 adrenergic receptors are known and described in the literature. Although the compounds in questions belong to different chemical classes (Idrugs 2001, 4(6), 662-76), some comprise a common 1H-imidazole type structural unit in their chemical structure. For example, the latter include compounds such as:
- 4-(1-indanylalkyl)—(WO 1051472);
- 4-(benzothienyl)—(WO 9951593);
- dihydro-indole—(FR 2735776);
- dihydro-indenyl—(EP 247764);
- 4-(5-fluoro-2,3-dihydro-1H-inden-2-yl)—(WO 9500492);
- 4(5)-(2-ethyl-2,3-dihydro-2-silainden-2-yl)—(Eur. J. Med. Chem. 1996, 31(9), 725-9;
- thieno[3,4-c]pyrroles (EP 599697);
- 4-(2-aryl- and -cycloalkyl-3,3,3-trifluoropropyl)—(EP 486385);
- 4-substitute-imidazole (J. Med. Chem. 1992, 35(4), 750-5);
- 4(5)-(2,2-diphenylethyl)—(Eur. J. Med. Chem. 1990, 25(7), 557-68);
- imidazole derivative (GB 2225782; EP 183492 and WO 9313074);
- 4-(5-fluoro-2,3-dihydro-1H-inden-2-yl)—(WO 9500492).

Of the compounds mentioned above, some only comprise relatively minimal structural differences. The most similar state of the art is represented by polycyclic indanylimidazole type compounds, claimed in the patent WO 0185698, complying with formula a below:

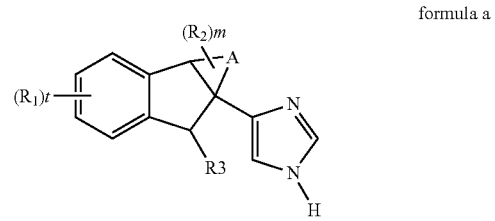

formula a wherein, among others:

A may form, with the two carbon atoms whereby it is attached, a 3-chain carbon-containing mono-cycle;

m may be 0 or 1;

$R_2$ may be a (C1-6)alkyl group t may be 0 or 1;

t is 1 and $R_1$ may be a halogen or a (C1-6)alkyloxy group;

R3 may be a hydrogen, OH, —O, (C1-6)alkyl or (C1-6)alkyloxy.

Therefore, the compounds represented above and the compounds according to the present invention are differentiated in the nature of the substituent in position 4 of the imidazole group, particularly by the presence of a 6-spiro-cyclopropane structural unit in the compounds according to the invention. Many structures comprising a 1H-imidazole group substituted in position 4 are already known for these alpha-2 adrenergic properties (see above). However, surprisingly, it appears that the substituent 6-spiro-1'-cyclopropane-1a,6-dihydro-1H-cyclopropa[a]inden-6a-yl gives the compounds according to the invention a very specific pharmacological profile.

In fact, we have demonstrated, in vitro:
an affinity of the compounds according to the invention with respect to the human alpha-2A subtype,
antagonistic or reverse agonistic properties of the compounds according to the invention on alpha-2A receptors.

In addition, we have demonstrated, in vivo, that the products according to the invention are capable of inhibiting the effect of scopolamine in a memory deficiency test. This test is considered as a representative animal model of the memory disorders arising in the course of Alzheimer's disease (Psychopharmacology 1992, 106, 26-30; Eur. J. Clin. Invest. 1998, 28, 944-9; Exp. Neurol. 2000, 163, 495-529). The compounds according to the invention, having such an activity profile, are therefore potentially useful for the treatment of diseases or disorders susceptible to the action of partial agonists, antagonists or reverse agonists of alpha-2 adrenergic receptors, particularly for the treatment of neurodegenerative diseases for which a significant therapeutic requirement exists.

Finally, the preparation method of the compounds according to the invention is different, that of the compounds claimed in the patent WO 0185698.

More specifically, the present invention relates to new 4-(6-spiro-1'-cyclopropane-1a,6-dihydro-1H-cyclopropa[a]inden-6a-yl)-1H-imidazole derivatives which, in their basic form, comply with the general formula 1:

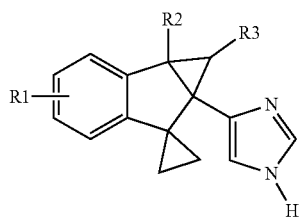

(1)

wherein:
R1 represents a hydrogen atom, a fluorine atom or a methoxyl group (OCH$_3$), the substituent R1 on the aromatic carbocycle possibly occupying the position 2, 3, 4 or 5;
R2 represents a hydrogen atom or a methyl group;
R3 represents a hydrogen atom, a methyl group or an ethyl group;
their addition salts and, if applicable, addition salt hydrates with pharmaceutically acceptable mineral acids or organic acids along with their tautomeric forms, enantiomers and enantiomer mixtures and stereoisomers, pure or in racemic mixtures or not.

In a particular embodiment of the invention, the compounds according to formula 1 wherein:
R1 and R2 have the same significance as above;
R3 represents a methyl group or an ethyl group;
the preferential stereoisomers of the products according to the invention are those wherein the R3 and 1H-imidazole substituents occupy either anti-periplanar positions or syn-periplanar positions with reference to the plane defined by the cyclopropanic nucleus.

The term anti-periplanar is used by the inventors to refer to the relative configurations of the molecules 1 for which the R3 and 1H-imidazole substituents are located on either side of the plane defined by the cyclopropanic nucleus. The term syn-periplanar is used by the inventors to refer to the relative configurations of the molecules 1 for which the R3 and 1H-imidazole substituents are located on the same side of the plane defined by the cyclopropanic nucleus.

The compounds according to the general formula 1 may exist in several tautomeric forms. Such tautomeric forms, although they are not explicitly reported in the present application to simplify the graphic representation of the developed formulas, are nevertheless included in the scope of the invention. The compounds according to the invention comprise several asymmetrical carbon atoms in their structure. For this reason, they exist in the form of enantiomers and diastereoisomers. The invention relates equally well to each pure stereoisomer, i.e. associated with less than 5% of another stereoisomer or a mixture of other stereoisomers, and mixtures of one or more stereoisomers in all proportions. Therefore, the compounds according to the invention may be used as pure stereoisomers or racemic or non-racemic stereoisomer mixtures.

Finally, the invention relates to the preparation method of derivatives according to general formula 1.

The derivatives according to general formula 1 may be obtained using the method described in the reaction diagram below.

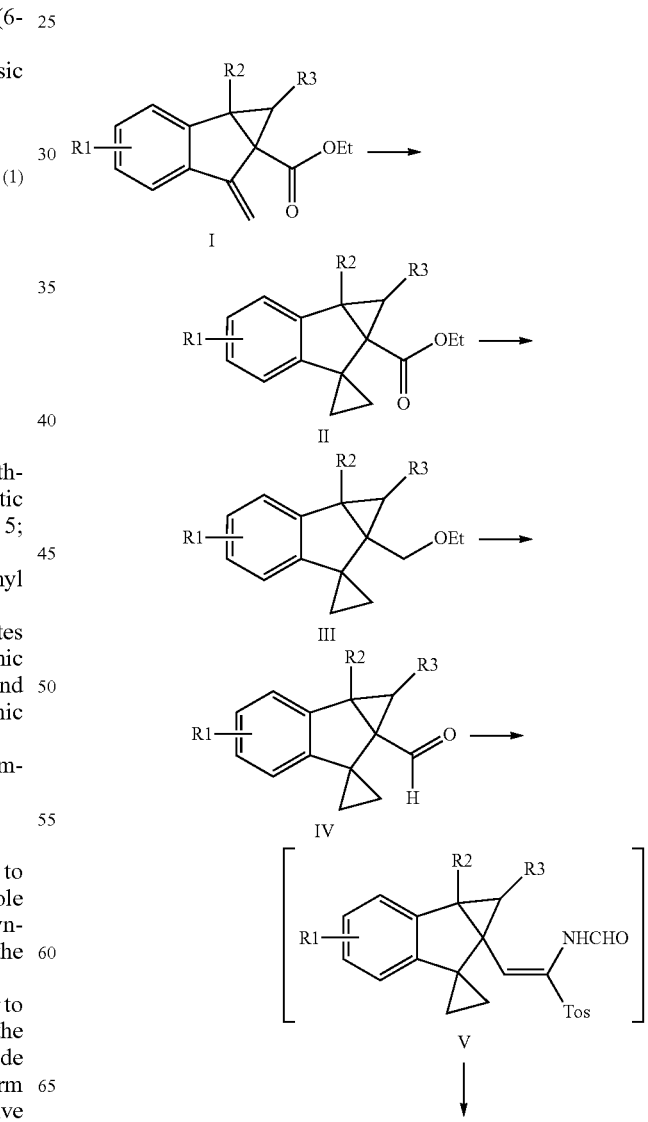

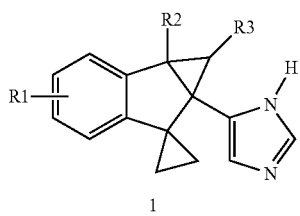

The preparation of the compounds according to the invention uses, as raw materials, the suitably substituted derivatives according to formula I, the synthesis method of which is described in the French patent application No. 0201839. A cyclopropanation reaction of the double bond, produced using a similar technique to that reported in Angew. Chem. Int. Ed. 2000, 39(24), 4539-42, results in the spiro derivative according to formula II. The ester function of the compound according to formula II is then reduced into the alcohol according to formula II by means of lithium borohydride in tetrahydrofuran according to a conventional organic chemistry method. The primary alcohol III is oxidised into the aldehyde according to formula IV by means of sulphur trioxide pyridine complex. The aldehyde IV is converted into the imidazole expected from formula 1, either in one step according to the method described in Heterocycles 1994, 39(1), 139-53; or via tosyl-formylamine according to formula V according to the method reported in Recl. Tray. Chim. Pays Bas 1979, 98(5), 258-62.

The invention also relates to pharmaceutical formulations containing, as the active ingredient, at least one of the derivatives according to general formula 1 or one of its salts or hydrates of its salts in combination with one or more inert substrates or other pharmaceutically acceptable vehicles.

The pharmaceutical formulations according to the invention may be, for example, formulations for oral, nasal, sublingual, rectal or parenteral administration. Examples of formulations for oral administration include tablets, capsules, granules, powders and solutions or oral suspensions.

The formulations suitable for the selected form of administration are known and described for example, in: Remington, The Science and Practice of Pharmacy, 19th edition, 1995, Mack Publishing Company.

The effective dose of a compound according to the invention varies according to numerous parameters such as, for example, the administration route selected, the weight, age, sex, state of progression of the disease to be treated and the susceptibility of the subject to be treated. As a result, the optimal dosage should be determined, according to the parameters deemed relevant, by the specialist in the field. Although the effective doses of a compound according to the invention may vary in wide proportions, the daily doses could range between 0.01 mg and 100 mg per kg of body weight of the subject to be treated. However, a daily dose of a compound according to the invention between 0.10 mg and 50 mg per kg of body weight of the subject to be treated is preferred.

The pharmaceutical formulations according to the invention are useful in the treatment of neurodegenerative diseases.

EXAMPLES

The following examples illustrate the invention, but do not limit it in any way.

In the examples and reference examples below:

(i) the progress of the reactions is monitored by means of thin layer chromatography (TLC) and, as a result, the reaction times are only mentioned as an indication;

(ii) different crystalline forms may give different melting points, the melting points reported in the present application are those of the products prepared according to the method described and are not corrected;

(iii) the structure of the products obtained according to the invention is confirmed by the nuclear magnetic resonance (NMR) and infrared (IR) spectra and centesimal analysis, the purity of the end products is verified by TLC, the enantiomeric purity of the reaction intermediates and the end products is determined by chiral phase HPLC;

(iv) the NMR spectra are recorded in the solvent specified. The chemical shifts (δ) are expressed in parts per million (ppm) with reference to tetramethylsilane. The multiplicity of the signals is specified by: s, singlet; d, doublet; t, triplet; q, quadruplet; m, multiplet; l, large.

(v) the different symbols of the units have their usual meaning: μg (microgram); mg (milligram); g (gram); ml (millilitre); mV (milliVolt); ° C. (degrees Celsius); mmole (millimole); nmole (nanomole); cm (centimetre); nm (nanometre); min (minute); ms (millisecond); Hz (hertz); [α](specific rotatory power measured at 589 nm, 25° C. and at the concentration c, in the present invention the dimension deg·cm$^2$·g$^{-1}$ is always understood); pressures are given in millibar (mb);

(vi) the abbreviations have the following meaning: F (melting point); Eb (boiling point); AUC (area under the curve);

(vii) the term "ambient temperature" refers to a temperature between 20° C. and 25° C.

Example 1

(6-spiro-1'-cyclopropane-1a,6-dihydro-1H-cyclopropa[a]inden-6a-yl)-ethyl carboxylate (II-1)

In the solution of 24.5 g (0.124 mole) of 2,4,6-trichlorophenol and 300 ml of dichloromethane under stirring and in nitrogen at −40° C., 113 ml (0.124 mole) of a toluene ZnEt$_2$ (1.1M) solution is added drop by drop. After 15 minutes of stirring at −40° C., 10 ml (0.124 mole) of diiodomethane is added and kept under stirring for 15 minutes before adding 6-methylene-1a,6-dihydro-1H-cyclopropa[a]inden-6a-ethyl carboxylate I-1, 13.22 g (0.062 mole). The suspension obtained is kept under stirring at ambient temperature overnight. After adding dichloromethane until completely dissolved, the solution is washed twice with 1N HCl followed by Na$_2$SO$_4$ and 0.5N NaOH (twice) and saline solution. The organic phase is dried on MgSO$_4$, filtered and the solvent is eliminated in a vacuum. The oil obtained is purified by silica gel chromatography using cyclohexane with 2% ethyl acetate as the eluent.

Yield: 89.8%

C$_{15}$H$_{16}$O$_2$: 228.29

$^1$H NMR (CDCl$_3$): 0.88 (m, 1H); 0.92 (m, 2H); 1.23 (t, 3H); 1.29 (m, 1H); 1.81 (dd, 1H); 2.35 (m, 1H); 3.17 (dd, 1H); 4.10 (d, 2H); 6.56 (m, 1H); 7.07 (m, 2H); 7.25 (m, 1H).

$^{13}$C NMR (CDCl$_3$): 14.15; 14.47; 17.16; 27.47; 29.21; 34.09; 34.16; 60.22; 118.97; 122.76; 125.40; 126.43; 142.46; 147.45; 171.84.

Example 2

(6-spiro-1'-cyclopropane-1a,6-dihydro-1H-cyclopropa[a]inden-6a-yl)-methanol (III-1)

The suspension of 13 g (0.234 mole) of KBH4, 10.5 g (0.239 mole) of LiCl and 100 ml of anhydrous THF is kept under stirring at ambient temperature for 1 hour. To this suspension, the solution of 12.71 g (0.056 mole) of (6-spiro-1'-cyclopropane-1a,6-dihydro-1H-cyclopropa[a]inden-6a-yl)-ethyl carboxylate (II-1) in 70 ml of anhydrous THF is added drop by drop and then reflux-heated under stirring for 4 hours. The suspension is vacuum-concentrated and the residue is treated with water. The product is extracted twice with ethyl acetate. The organic phase is washed with saline solution, dried on MgSO4, filtered and vacuum-concentrated. The unprocessed oil is purified by silica gel chromatography using cyclohexane with 20% ethyl acetate as the eluent.

Yield: 85%

$C_{13}H_{14}O$: 186.25

$^1$H NMR (CDCl$_3$): 0.64 (t, 1H); 0.96 (m, 2H); 1.17 (m, 2H); 1.25 (t, 1H, exchangeable with D$_2$O); 1.54 (m, 1H); 2.49 (q, 1H); 3.56 (dd, 1H, (d, after exchange with D$_2$O)); 3.74 (dd, 1H, (d, after exchange with D$_2$O)); 6.58 (m, 1H); 7.06 (m, 2H); 7.25 (m, 1H).

Example 3

(6-spiro-1'-cyclopropane-1a,6-dihydro-1H-cyclopropa[a]inden-6a-yl)-carboxaldehyde (IV-1)

In the solution of 1.2 g (6.44 mmoles) of (6-spiro-1-cyclopropane-1a,6-dihydro-1H-cyclopropa[a]inden-6a-yl)-methanol (III-1) and 6 ml of anhydrous DMSO, 2.7 ml (19.4 mmoles) of triethylamine is added. The mixture obtained is placed under stirring on a chilled water bath and pyridine-SO$_3$ complex is added in 3.1 g (19.4 mmoles) fractions. After 4 hours of stirring at ambient temperature, the solution is poured into chilled water. The product is extracted twice with ethyl acetate. The organic phase is washed with an aqueous citric acid solution and then with saline solution. After drying on MgSO$_4$ and filtration, the solvent is eliminated at reduced pressure. The residual oil obtained is used without any other purification in the subsequent step.

$C_{13}H_{12}O$: 184.23

$^1$H NMR (CDCl$_3$): 0.97-1.03 (m, 2H); 1.15 (t, 1H); 1.23 (m, 1H); 2.01 (dd, 1H); 2.37 (m, 1H); 3.15 (dd, 1H); 6.62 (d, 1H); 7.12 (m, 2H); 7.26 (t, 1H); 9.26 (s, 1H).

Example 4

4-(6-spiro-1'-cyclopropane-1a,6-dihydro-1H-cyclopropa[a]inden-6a-yl)-1H-imidazole (1-1)

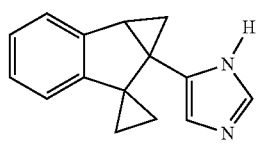

In the suspension of 1.18 g (6.4 mmoles) of (6-spiro-1'-cyclopropane-1a,6-dihydro-1H-cyclopropa[a]inden-6a-yl)-carboxaldehyde (IV-1), 1.25 g (6.4 mmoles) of para-tolylsulfonylmethyl isocyanide and 15 ml of absolute ethanol under stirring at ambient temperature, 40 mg of sodium cyanide is added. After 1 hour of stirring at ambient temperature, the majority of the ethanol is eliminated at reduced pressure. To the residue, 20 ml of methanol ammonia (4N) solution is added and the solution obtained is maintained at 90° C. for 16 hours. After returning to ambient temperature, the brown solution obtained is heated to dryness at reduced pressure. The residue is taken up with ethyl acetate and the insolubles are filtered. The mother liquors are extracted twice with 1N hydrochloric acid. The acidic aqueous phase are washed with ether and then alkalinised. The product is extracted twice with ethyl acetate. The organic phases are washed with saline solution, dried on MgSO$_4$, filtered and the solvent is eliminated at reduced pressure. The residue is purified by silica chromatography using chloroform with 3% methanol as the eluent.

Yield: 28.8%

$C_{15}H_{14}N_2$: 222.28

Fumarate of compound in title, F: 218-220° C.

Elementary analysis, $C_{19}H_{18}N_2O_4$: 338.36

Calculated: C, 67.45%; H, 5.36%; N, 8.28%.

Found: C, 67.17%; H, 5.36%; N, 8.15%.

$^1$H NMR (DMSOd$_6$): 0.61 (t, 1H); 0.79 (m, 2H); 0.94 (m, 1H); 1.09 (m, 1H); 1.46 (dd, 1H); 2.71 (dd, 1H); 6.62 (s, 2H); 6.68 (m, 1H); 6.90 (s, 1H); 7.06 (m, 2H); 7.28 (m, 1H); 7.63 (s, 1H).

The compounds according to formula 1-1 are split by liquid chromatography on CHIRALCEL OD substrate.

Example 5

(+)-4-(6-spiro-1'-cyclopropane-1a,6-dihydro-1H-cyclopropa[a]inden-6a-yl)-1H-imidazole (+)-(1-1)

Fumarate of compound in title, F: 168-170° C.

$[\alpha]^{25}_D$=+50.5° (c=0.334, CH$_3$OH)

Elementary analysis, $C_{16}H_{18}N_2O_4$: 338.36

Calculated: C, 67.45%; H, 5.36%; N, 8.28%.

Found: C, 67.24%; H, 5.39%; N, 8.12%.

Example 6

(−)-4-(6-spiro-1'-cyclopropane-1a,6-dihydro-1H-cyclopropa[a]inden-6a-yl)-1H-imidazole (−)-(1-1)

Fumarate of compound in title, F: 170-172° C.

$[\alpha]^{25}_D$=−47.75° (c=0.295, CH$_3$OH)

Elementary analysis, $C_{19}H_{18}N_2O_4$: 338.36

Calculated: C, 67.45%; H, 5.36%; N, 8.28%.

Found: C, 67.23%; H, 5.36%; N, 8.16%.

Example 7

4-(1-exo-methyl-6-spiro-1'-cyclopropane-1a,6-dihydro-1H-cyclopropa[a]inden-6a-yl)-1H-imidazole (1-2)

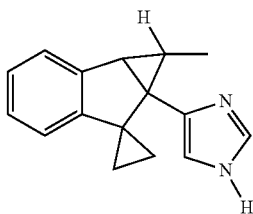

Using 1-exo-methyl-6-methylene-1a,6-dihydro-1H-cyclopropa[a]inden-6a-ethyl carboxylate (I-2) as the starting product and following the procedure described in examples 1-4, the compound in the title is obtained.

Fumarate of compound in title, F: 203-205° C.

Elementary analysis, $C_{20}H_{20}N_2O_4$: 352.39

Calculated: C, 68.17%; H, 5.72%; N, 7.95%.

Found: C, 68.69%; H, 5.90%; N, 8.07%.

$^1$H NMR (DMSOd$_6$): 0.57 (m, 1H); 0.65 (m, 1H); 0.88 (s, 3H); 0.92 (m, 1H); 1.28 (m, 1H); 2.54 (d, 1H, J=1.6 Hz); 6.61 (s, 2H); 6.63 (m, 1H); 6.68 (s, 1H); 7.04 (m, 2H); 7.28 (m, 1H); 7.66 (s, 1H).

Example 8

4-(1-endo-ethyl-6-spiro-1'-cyclopropane-1a,6-dihydro-1H-cyclopropa[a]inden-6a-yl)-1H-imidazole (1-3)

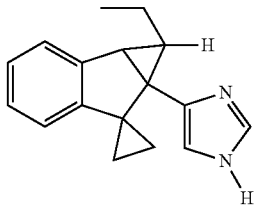

Using (1-endo-ethyl-6-methylene-1a,6-dihydro-1H-cyclopropa[a]inden-6a-ethyl carboxylate (I-3), itself obtained from (Z)-2-(1-butenyl)-benzoic acid (RN 129780-54-7), as the starting product and following the procedure described in examples 1-4, the compound in the title is obtained.

Fumarate of compound in title, F: 179-181° C.

Elementary analysis, $C_{21}H_{22}N_2O_4$: 366.42

Calculated: C, 68.84%; H, 6.05%; N, 7.64%.

Found: C, 68.36%; H, 5.99%; N, 7.63%.

$^1$H NMR (D$_2$O): 0.62 (m, 1H); 0.86 (t, 3H); 0.95 (m, 2H); 1.14 (m, 1H); 1.20 (m, 1H); 1.38 (m, 1H); 1.74 (m, 1H); 3.03 (d, 1H, J=8.8 Hz); 6.66 (s, 2H); 6.75 (m, 1H); 7.21 (m, 2H); 7.31 (s, 1H); 7.39 (m, 1H); 8.56 (s, 1H)

Example 9

4-(1a-methyl-6-spiro-1'-cyclopropane-1a,6-dihydro-1H-cyclopropa[a]inden-6a-yl)-1H-imidazole (1-4)

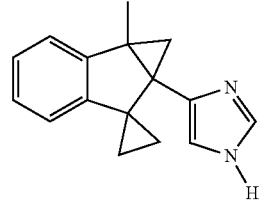

Using (1a-methyl-6-methylene-1a,6-dihydro-1H-cyclopropa[a]inden-6a-yl)-ethyl carboxylate (I-4), itself obtained from 2-isopropenyl benzoic acid (RN 3609-46-9), as the starting product and following the procedure described in examples 1-4, the compound in the title is obtained.

Example 10

4-(4-fluoro-6-spiro-t-cyclopropane-1a,6-dihydro-1H-cyclopropa[a]inden-6a-yl)-1H-imidazole (1-5)

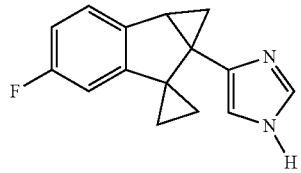

Using (4-fluoro-6-methylene-1a,6-dihydro-1H-cyclopropa[a]inden-6a-yl)-ethyl carboxylate (I-5) as the starting product and following the procedure described in examples 1-4, the compound in the title is obtained.

Fumarate of compound in title, F: 214-216° C.

Elementary analysis, $C_{19}H_{17}N_2FO_4$: 356.35

Calculated: C, 64.04%; H, 4.811; N, 7.86%.

Found: C, 63.87%; H, 4.88%; N, 7.81%.

$^1$H NMR (DMSO-d$_6$): 0.60 (t, 1H); 0.83 (m, 2H); 0.98 (m, 1H); 1.09 (m, 1H); 1.42 (dd, 1H); 2.68 (dd, 1H); 6.56 (d, 1H); 6.66 (s, 2H); 6.83 (m, 1H); 6.88 (s, 1H); 7.27 (m, 1H); 7.59 (m, 1H).

The compounds according to formula 1 and their therapeutically acceptable salts offer properties of pharmacological interest.

The results of the tests are given in the table below:

| Compound | Affinity (pKi) Alpha-2A | Intrinsic activity % stimulated | Scopolamine memory deficiency % aplitude of effect (dose, mg/kg i.p.) |
|---|---|---|---|
| 1-1 | 9.5 | +14 | +122 (2.5) |
| (-)-1-1 | 8.6 | +37 | +138 (2.5) |
| 1-2 | 8.1 | +7 | +201 (0.63) |
| 1-5 | 9.5 | −10 | +241 (0.63) |
| (-)-adrenaline | — | +100 | — |
| Donepezil | — | — | +67 (0.16) |

Bonds with Alpha-2 Adrenergic Receptors

The C6 cell membranes continuously expressing the human alpha-2A receptor are prepared in Tris-HCl (pH=7.6).

The bond tests are conducted with 2 nM [$_3$H]RX 821002. The incubation medium consists of 0.4 ml of cell membranes (10 µg of proteins), 0.05 ml of radioligand and 0.05 ml of test product or phentolamine (10 µM) to determine the non-specific bond. The reaction is stopped after 30 minutes of incubation at 25° C. by adding 3 ml of Tris-HCl, 50 mM (pH=7.6), cold, followed by filtration on Whatman filters, GF/B using a Brandel. The Ki values are calculated according to the equation $Ki=IC_{50}/(1+C/Kd)$ where C is the concentration and Kd the dissociation constant, $pKi=-\log Ki$. Under these conditions, the compounds according to the invention appear to have a strong affinity for human alpha-2A adrenergic subtype receptors.

Measurement of Alpha-2 Adrenergic Receptor Activation

The GTPγS responses are produced on membrane preparations in 20 mM HEPES (pH=7.4) with 30 [mu]M of GDP, 100 mM of NaCl, 3 mM of $MgCl_2$ and 0.2 mM of ascorbic acid. The maximum GTPγS stimulation is determined in the presence of 10 mM of (−)-adrenaline and calculated with respect to the basal GTPγS response. The results are expressed with reference to adrenaline or RX 811059. Under these conditions, the compounds according to the invention are distinguished from the majority of the compounds according to the prior art in that they behave more like reverse agonists on human alpha-2A adrenergic receptors (see table above).

Scopolamine-Induced Memory Deficiency Test.

Scopolamine has amnesiac properties in animals and humans. In this way, its administration to healthy humans induces certain symptoms similar to those observed in Alzheimer's disease. Therefore, the scopolamine-induced memory deficiency is used as an experimental pharmacological model of the memory disorders observed in the course of this condition. Scopolamine reduces acquisition, memorisation and recall capacities in a passive avoidance test in rats. It consists of measuring the hesitancy, after learning, shown by an animal to enter a dark compartment in which it receives a low-intensity electric shock. The administration of scopolamine does away with this hesitancy and the compounds studied inhibit the effect of scopolamine. The experimental protocol used is described in Psychopharmacol. 1992, 106, 26-30.

The compounds according to the invention show a high activity (see table above). The amplitude of the effect obtained with the compounds according to the invention is greater than that, for example, of donezepil, an acetylcholinesterase inhibitor used in clinical practice for the treatment of Alzheimer's disease (Chem. Rec. 2001, 1(1), 63-73). Therefore, the compounds according to the invention are capable of effectively inhibiting the memory deficiency induced by scopolamine.

Therefore, the results of the tests demonstrate that the compounds according to the formula 1:
- have a strong affinity for human alpha-2A subtype adrenergic receptors;
- generally behave as partial agonists or antagonists or reverse agonists on human alpha-2A adrenergic receptors;
- are active, in vivo, in an animal model considered to be representative of the memory disorders observed in the course of Alzheimer's disease.

For this reason, the compounds according to their invention and their therapeutically acceptable salts are potentially useful as medicinal products, particularly in the treatment of some progressive neurodegenerative diseases, such as Alzheimer's disease, for example.

The compounds according to the invention may be administered by the oral, nasal, sublingual, rectal or parenteral route. As a non-limitative example of a formulation, a preparation of the compounds according to the invention is given below. The ingredients and other therapeutically acceptable substances may be introduced in other proportions without modifying the scope of the invention. The terms 'active ingredient' used in the formulation example below refer to a compound according to formula 1 or an addition salt or, if applicable, an addition salt of the compound according to formula 1 with a pharmaceutically acceptable mineral acid or organic acid.

Example 11

Pharmaceutical Formulation

Preparation formula for 1000 tablets each containing 10 mg of active ingredient consisting of at least one imidazolic compound according to the invention:
Active ingredient 10 g
Lactose 100 g
Cornstarch 10 g
Magnesium stearate 3 g
Talc 3 g Example 12

Spatial Working Memory and Visuospatial Perception in Parkinson's Disease (PD)

Impairment of spatial working memory and visuospatial perception in patients with Parkinson's disease (PD) is well documented in the scientific literature (e.g., Postle B R, Jonides J, Smith E E, Corkin S, Growdon J H. (1997b) *Spatial, but not object, delayed response is impaired in early Parkinson's disease*. Neuropsychology. 11:171-179; Postle B R, Locascio J J, Corkin S, Growdon J H. (1997a) *The time course of spatial and object learning in Parkinson's disease*. Neuropsychologia. 35 1413-1422.

Morris Water Maze Test and its Pertinence to Spatial Memory Deficits in PD

The Morris water maze is a test used to measure spatial working memory in rats, as originally described by Morris (Morris R. G. M. (1981) *Spatial localization does not require the presence of local cues*. Learn. Motiv. 12: 239-260). Basic features of this test have in fact been incorporated into the clinical setting and have been shown to be sensitive for revealing spatial memory deficits in PD patients (Leplow B, Höll D, Zeng L, Herzog A, Behrens K, Mehdorn M. (2002) *Spatial behaviour is driven by proximal cues even in mildly impaired Parkinson's disease*. Neuropsychologia. 40:1443-55).

Morris Water Maze—Basic Principles of the Test

In the animal test paradigm, rats are placed into a circular pool containing water and are required to find an escape platform just beneath the surface of the water and therefore invisible to the animal. The performances are dependent on the number of training days. In a probe trial without platform, 24 hours after three or 4 training days, rats spend significantly more than 25% of their time (chance performance) in the quadrant that contained the platform during the training sessions, indicating that they have learned the location of the platform in this quadrant. However, after only 1 or 2 training days, equal time is spent in all the four quadrants of the pool, suggesting that rats have not learned the platform location. Since, after two training days, the spatial memory performance of control animals are not significant, a potential promnesic effect of a compound can be detected.

Morris Water Maze—Detailed Protocol

The water maze test was adapted from the original protocol of Morris (1981). The test apparatus consisted of a circular fibreglass tank (130 cm in diameter, 50 cm deep). The pool was filled to a height of 30 cm with water at room temperature (21-22° C.). The pool was divided into four virtual quadrants (Q1, Q2, Q3 and Q4) of equal surface area. A transparent escape platform made of Plexiglas (10 cm in diameter, 29 cm high) was placed in a fixed location in the tank, 1 cm below the water surface. The platform was not visible from just above water level (Gage F. H., Kelly P. A. T., Björklund A. (1984) *Regional changes in brain glucose metabolism reflect cognitive impairments in aged rats*. J Neurosci 4: 2856-2865) and transfer trials have indicated that escape onto the platform was not achieved by visual or other proximal cues (Morris, 1981). Many extra-maze cues surrounded the maze and were available for the rats to use in locating the escape platform. On the training trials, the platform remained in a constant location in the centre of one quadrant (Q4) equidistant from the centre and the edge of the pool. Each rat received three trials/day for 1, 2, 3 or 4 days. Each training trial involved placing the rat into the pool facing the wall at one of the 3 quadrants Q1, Q2 and Q3. A different starting point was randomly used on each trial. The rats were allowed to swim freely until they found the escape platform. The latency to find the hidden platform was recorded and used as a measure of acquisition of the task. If a rat failed to locate the platform within 100 sec, it was then manually guided to the escape platform by the experimenter. The intertrial interval was 20 sec during which the rat remained on the platform. Twenty hours after the last training trial, the platform was removed from the pool, the rats were allowed to swim for 60 sec in the pool and the time spent in the target quadrant Q4 (the quadrant in which the platform was during training) was recorded. The percent time spent in the previous training quadrant Q4 was used as an index of memory. The higher the percentage, the better the memory was considered to be (Yavich L., Sirviö J., Haapalinna A., Puumala T., Koivisto E., Heinonen E., Riekkinen P. Jr. (1996) *The systemic administration of tacrine or selegeline facilitate spatial learning in aged Fisher 344 rats*. J Neural Transm 103: 619-626).

Pharmacological Treatment and Statistical Analysis

Rats received two training days and were tested in a probe trial, without platform, on the third day. Compounds 1-1 (Example 4), (−)-1-1 (Example 6), (+)-1-1 (Example 5) and 1-2 (Example 7) were administered to the rats by intraperitoneal (i.p.) injection immediately after the training sessions of days 1 and 2 to study the potential promnesic effects of these compounds. Results were expressed as the mean±standard error of the mean (SEM) of performance (latency to find the platform and percentage time spent in target quadrant) and were analysed by one-way analysis of variance, with drug treatment as the factor, followed by a 2-tailed Student t-test (GB-STAT, Friedman P. (1991) GB-STAT: computer aided statistics & graphics, Ver 3.0. Dynamic Microsystems, Inc., Silver Spring). In the probe trial, without platform, results were also compared to chance performance (25%) by a 1-sample Student t-test (GB-STAT, Friedman, 1991). Results obtained with compounds I-1 (Example 4), (−)-1-1 (Example 6), (+)-1-1 (Example 5) and 1-2 (Example 7):

In the probe trial, 24 hours after two training days, rats that had been treated with compound I-1, compound (−)-1-1, compound (+)-1-1 and compound I-2 immediately after the training sessions, showed a significant increase in their spatial memory performance on day 3. Thus, compound I-1, at a dose of 2.5 mg/kg i.p., increased spatial memory performance by 46%; compound (−)-1-1, at the dose of 0.63 and 2.5 mg/kg i.p., increased performance by up to 48%; compound (+)-1-1, at a dose of 0.16 mg/kg i.p., increased performance by 17% and compound I-2, at a dose of 2.54 mg/kg i.p. increased performance by 42%.

Interpretation of Results Obtained

It is concluded that compounds I-1, (−)-1-1, (+)-1-1 and 1-2 all have a promnesic effect, as revealed in this animal test, by facilitating the spatial memory processes.

What we claim is:

1. A method of treating a memory deficiency associated with Parkinson's disease in a subject in need of such treatment, said method comprising administering to said subject an effective amount of a compound of formula (I):

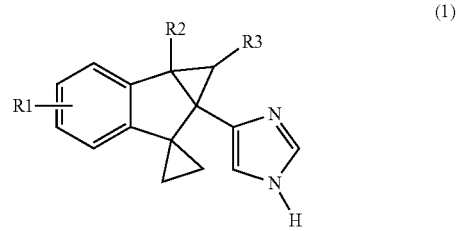

wherein:
R1 represents a hydrogen atom, a fluorine atom or a methoxyl group ($OCH_3$), the substituent R1 on the aromatic carbocycle occupying the position 2, 3, 4 or 5;
R2 represents a hydrogen atom or a methyl group;
R3 represents a hydrogen atom, a methyl group or an ethyl group;
or an addition salt with a pharmaceutically acceptable mineral acid or organic acid, or enantiomers, diastereoisomers or tautomer thereof.

2. The method according to claim 1, wherein the compound of formula (1) comprises the R3 and 1H-imidazole substituents occupying syn-periplanar positions with reference to the plane defined by the cyclopropanic nucleus, R1 and R2 are as defined in claim 1, and R3 is a methyl group ($CH_3$) or an ethyl group ($CH_2CH_3$).

3. The method according to claim 1, wherein the compound of formula (1) is the levogyral enantiomer or the dextrogyral enantiomer.

4. A method of treating a memory deficiency associated with Parkinson's disease in a subject in need of such treatment, said method comprising administering to said subject an effective amount of at least one compound selected from the group consisting of:
4-(6-spiro-1'-cyclopropane-1a,6-dihydro-1H-cyclopropa[a]inden-6a-yl)-1H-imidazole;
4-(2-fluoro-6-spiro-1'-cyclopropane-1a,6-dihydro-1H-cyclopropa[a]inden-6a-yl)-1H-imidazole;
4-(3-fluoro-6-spiro-1'-cyclopropane-1a,6-dihydro-1H-cyclopropa[a]inden-6a-yl)-1H-imidazole;
4-(4-fluoro-6-spiro-1'-cyclopropane-1a,6-dihydro-1H-cyclopropa[a]inden-6a-yl)-1H-imidazole;
4-(5-fluoro-6-spiro-1'-cyclopropane-1a,6-dihydro-1H-cyclopropa[a]inden-6a-yl)-1H-imidazole;
4-(1-exo-methyl-6-spiro-1'-cyclopropane-1a,6-dihydro-1H-cyclopropa[a]inden-6a-yl)-1H-imidazole;
4-(1-exo-methyl-2-fluoro-6-spiro-1'-cyclopropane-1a,6-dihydro-1H-cyclopropa[a]inden-6a-yl)-1H-imidazole;
4-(1-exo-methyl-3-fluoro-6-spiro-1'-cyclopropane-1a,6-dihydro-1H-cyclopropa[a]inden-6a-yl)-1H-imidazole;

4-(1-exo-methyl-4-fluoro-6-spiro-1'-cyclopropane-1a,6-dihydro-1H-cyclopropa[a]inden-6a-yl)-1H-imidazole;

4-(1-exo-methyl-5-fluoro-6-spiro-1'-cyclopropane-1a,6-dihydro-1H-cyclopropa[a]inden-6a-yl)-1H-imidazole;

4-(1-endo-ethyl-6-spiro-1'-cyclopropane-1a,6-dihydro-1H-cyclopropa[a]inden-6a-yl)-1H-imidazole; and 4-(1a-methyl-6-spiro-1'-cyclopropane-1a,6-dihydro-1H-cyclopropa[a]inden-6a-yl)-1H-imidazole;

and the addition salts with pharmaceutically acceptable mineral acids or organic acids, and the enantiomers, diastereoisomers and tautomers thereof.

5. The method according to claim 4, wherein said at least one compound is selected from the group consisting of:

4-(6-spiro-1'-Cyclopropane-1a,6-dihydro-1H-cyclopropa[a]inden-6a-yl)-1H-imidazole;

(−)-4-(6-spiro-1'-Cyclopropane-1a,6-dihydro-1H-cyclopropa[a]inden-6a-yl)-1H-imidazole;

4-(4-fluoro-6-spiro-1'-cyclopropane-1a,6-dihydro-1H-cyclopropa[a]inden-6a-yl)-1H-imidazole; and 4(1-exo-methyl-6-spiro-1'-cyclopropane-1a,6-dihydro-1H-cyclopropa[a]inden-6a-yl)-1H-imidazole.

6. The method according to claim 4, wherein said at least one compound is 4-(6-spiro-1'-Cyclopropane-1a,6-dihydro-1H-cyclopropa[a]inden-6a-yl)-1H-imidazole.

7. The method according to claim 4, wherein at least one compound selected from the group of compounds is the levogyral enantiomer or the dextrogyral enantiomer.

* * * * *